(12) United States Patent
Kao

(10) Patent No.: US 7,087,019 B2
(45) Date of Patent: Aug. 8, 2006

(54) APPARATUS FOR TESTING SKIN MOISTURE

(76) Inventor: Han-Chin Kao, 12F-3, #130 Chi Ho Rd., Taipei (TW)

( * ) Notice: Subject to any disclaimer, the term of this patent is extended or adjusted under 35 U.S.C. 154(b) by 0 days.

(21) Appl. No.: 10/758,079

(22) Filed: Jan. 16, 2004

(65) Prior Publication Data

US 2005/0159655 A1    Jul. 21, 2005

(51) Int. Cl.
*A61B 5/00* (2006.01)
*A61B 5/05* (2006.01)
*A61B 5/04* (2006.01)
*G01R 27/26* (2006.01)
*G01R 27/08* (2006.01)

(52) U.S. Cl. .............. 600/306; 600/307; 600/547; 600/372; 324/664; 324/689; 324/692; 324/694

(58) Field of Classification Search ........... 600/306, 600/307, 547, 372; 324/664, 689, 692, 694, 324/696; 73/73, 74
See application file for complete search history.

(56) References Cited

U.S. PATENT DOCUMENTS

| | | | | |
|---|---|---|---|---|
| 4,066,068 A | * | 1/1978 | Nilsson et al. | 600/307 |
| 4,966,158 A | * | 10/1990 | Honma et al. | 600/547 |
| 5,001,436 A | * | 3/1991 | Scot et al. | 324/689 |
| 5,131,390 A | * | 7/1992 | Sakaguchi et al. | 600/346 |
| 5,755,672 A | * | 5/1998 | Arai et al. | 600/547 |
| 5,961,471 A | * | 10/1999 | Nickson | 600/546 |
| 6,287,255 B1 | * | 9/2001 | Endo et al. | 600/307 |
| 6,370,426 B1 | * | 4/2002 | Campbell et al. | 600/547 |
| 6,533,725 B1 | * | 3/2003 | Endo et al. | 600/306 |
| 2002/0137992 A1 | * | 9/2002 | Lahtinen | 600/307 |

* cited by examiner

*Primary Examiner*—Robert L. Nasser
*Assistant Examiner*—Navin Natnithithadha
(74) *Attorney, Agent, or Firm*—Troxell Law Office, PLLC

(57) ABSTRACT

An apparatus for testing skin moisture including a casing, a fixed base at the front end of the casing, at least one through hole on the fixed base, a hollow cylindrical metal electrode with a closed end passing through the through hole, and an electrically conductive elastic member in the electrode. The elastic member pressing between the electrode on a first end and is fixed to the casing at a second end. The casing has a correction resistor coupled in parallel with the elastic member. The correction resistor is coupled to a micro alternate current generator, and an alternate current resistance measuring circuit is coupled to a CPU single-chip microprocessor. A measured value of resistance is compared with a predetermined value stored in a memory by a CPU single-chip microprocessor, the result of the comparison is displayed by a display device.

3 Claims, 6 Drawing Sheets

APPARATUS FOR TESTING SKIN MOISTURE

FIELD OF THE INVENTION

The present invention relates to an apparatus for testing skin moisture, more particularly pertains to a skin moisture tester making use of the restriction of a fixed base to keep a constant moving distance between the electrodes, such that the elastic members on the electrodes exert the same pressure on the electrodes, and the electrodes exert the same pressure on skin, and thus the same test result can be obtained under the same testing environment.

BACKGROUND OF THE INVENTION

Please refer to FIG. 1 for the conventional instrument for testing skin moisture. Such instrument comprises a portable casing 100, a ceramic resonator 110 at the front end of the casing 100, a liquid crystal display (LCD) screen 120 on the surface of the casing 100, and a testing circuit inside the casing 100; wherein the testing circuit is coupled to the ceramic resonator 110 and the LCD screen 120. In the test, such device makes use of the ceramic resonator 110 to contact with the skin, which will cause a change of resonance frequency. The measured difference will be sent to the testing circuit for data processing, and the water content of the testing skin can be calculated. The result of such calculation will be displayed on the LCD screen 120, so that the user can know about the test result. However, the manufacturing cost of the ceramic resonator 110 is higher than that of the conventional testing components, and the traditional skin moisture test involves individual requirements and cost to customize the ceramic resonator 110 for the instrument.

In view of the shortcomings of the traditional structure, the inventor of this invention focused on the problem to provide a feasible solution, and conducted extensive research and development, and finally invented the apparatus for testing skin moisture in accordance with this invention.

SUMMARY OF THE INVENTION

The primary objective of the present invention is to provide an apparatus for testing skin moisture, which comprises a casing, a fixed base at the front end of the casing, at least one through hole on the fixed base, a hollow cylindrical metal electrode with a closed end passing through the through hole, and an electrically conductive elastic member in the electrode; wherein the elastic member is pressed into the electrode, the other end of the elastic member is fixed into the casing, and the casing has a correction resistor coupled in parallel with the elastic member, and the correction resistor is coupled to a micro alternate current generator, and an alternate current resistance measuring circuit is coupled to a CPU single-chip microprocessor. In the test, the electrodes are pressed onto the skin of the person taking the test, so that a resistance can be measured when a micro alternate current of the electrode passes through the skin. After the measured value of this resistance is compared with a predetermined value of the data stored in a memory by the CPU single-chip microprocessor, the result of the comparison will be displayed by a display device. As the electrodes press on the skin and move towards the casing, the limitation of the fixed base keeps the moving distance the same for each time, and thus the electrodes can exert the same pressure on the skin. Under the same testing environment, the same result is obtained, and the test will not give different results due to different pressures exerted by the electrodes. Since this invention makes use of the electrodes for the test, therefore the cost is much lower than that for the traditional instruments.

Another objective of this invention is to provide an apparatus for testing skin moisture, which comprises a power supply in its casing, and the power supply is coupled to an elastic member with a circuit, a micro alternate current generator, and an alternate current resistor, so that before the test is taken, the micro alternate current passes through the correction resistor in parallel with the electrode to produce a resistance which confirms whether or not the operation of the apparatus of this invention is normal and corrects the basic testing value in the database. Such arrangement can prevent errors before the test is taken.

DETAILED DESCRIPTION OF THE PREFERRED EMBODIMENTS

Figure 1:
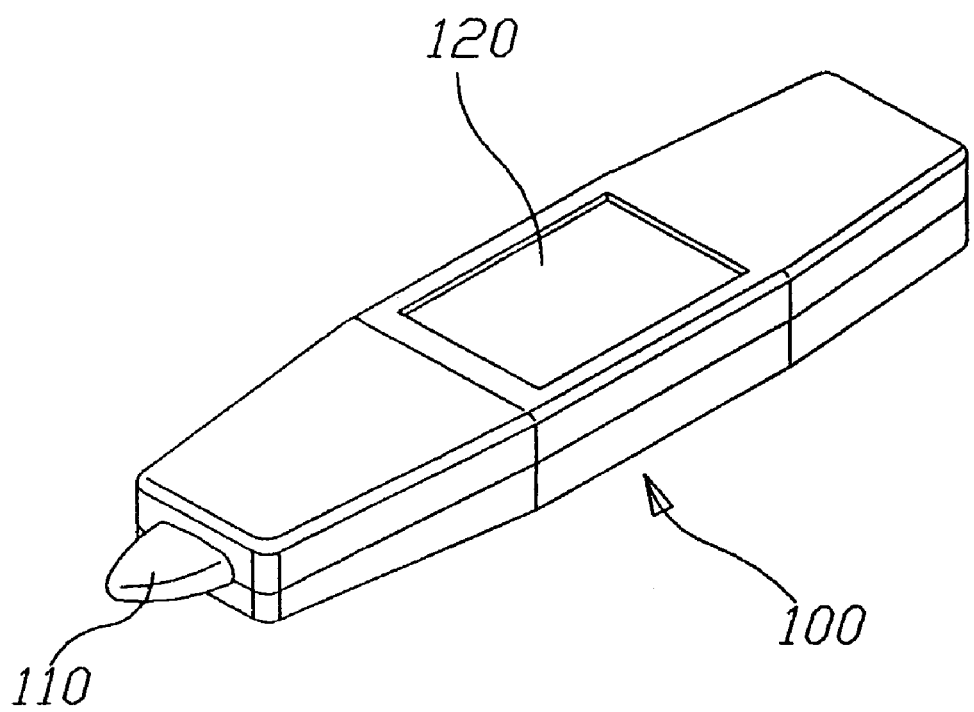
FIG. 1 is a perspective diagram of the prior-art device.
Figure 2:
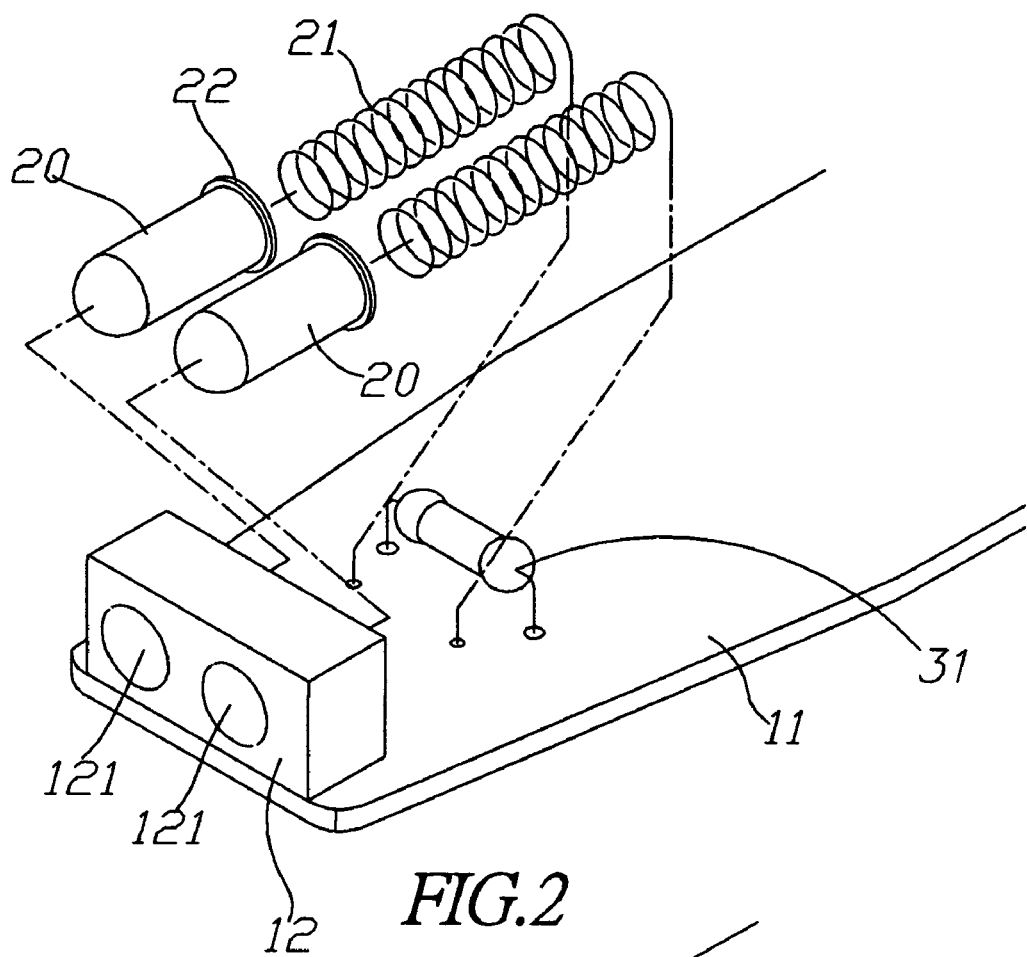
FIG. 2 is a perspective diagram of the disassembled parts of the structure showing the electrode being installed onto the casing according to a preferred embodiment of this invention.
Figure 3:
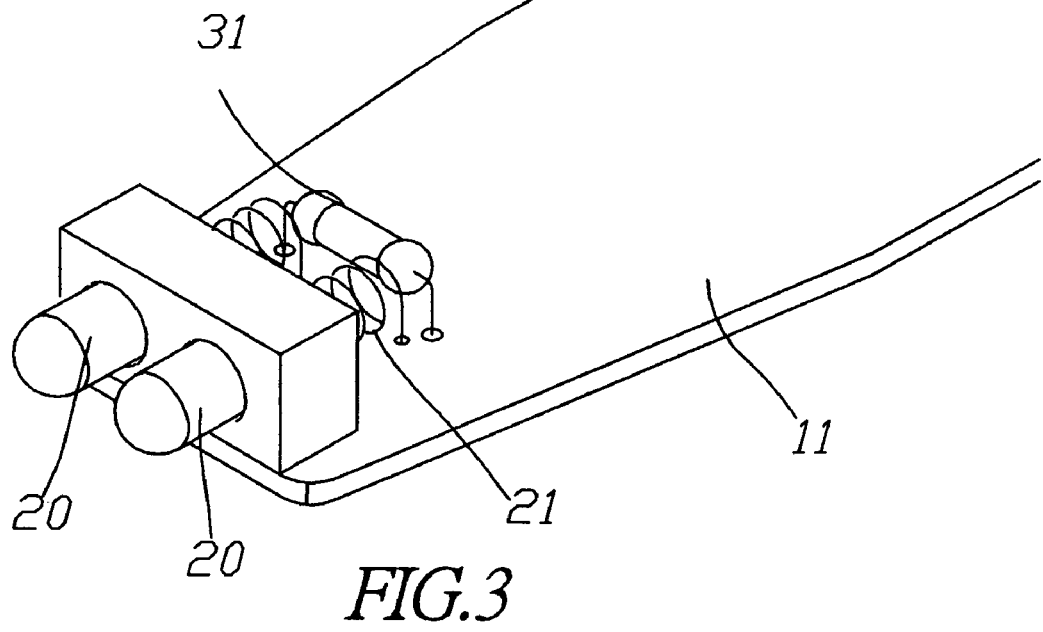
FIG. 3 is a perspective diagram of the assembled structure showing the electrode being installed onto the casing according to a preferred embodiment of this invention.
Figure 4:
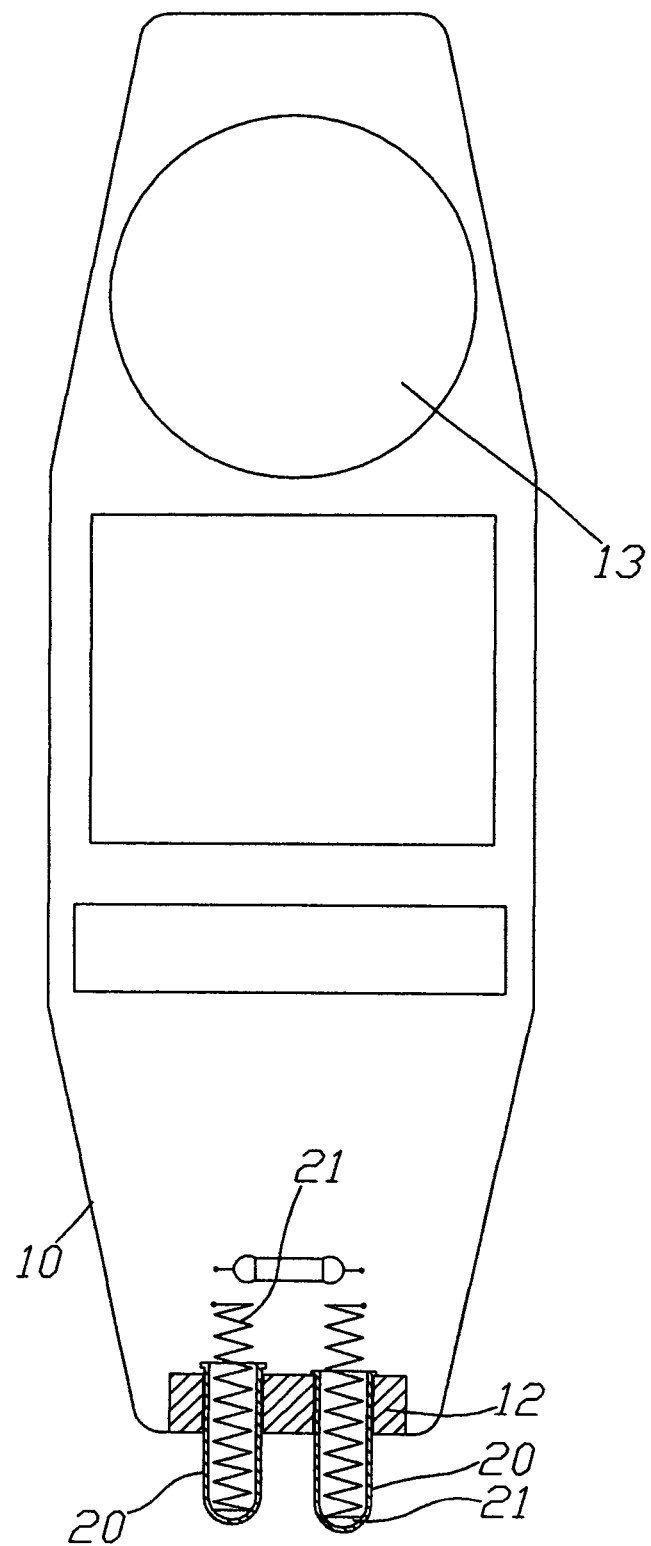
FIG. 4 is a cross-sectional diagram of the electrode being installed onto the casing according to a preferred embodiment of this invention.
Figure 5:
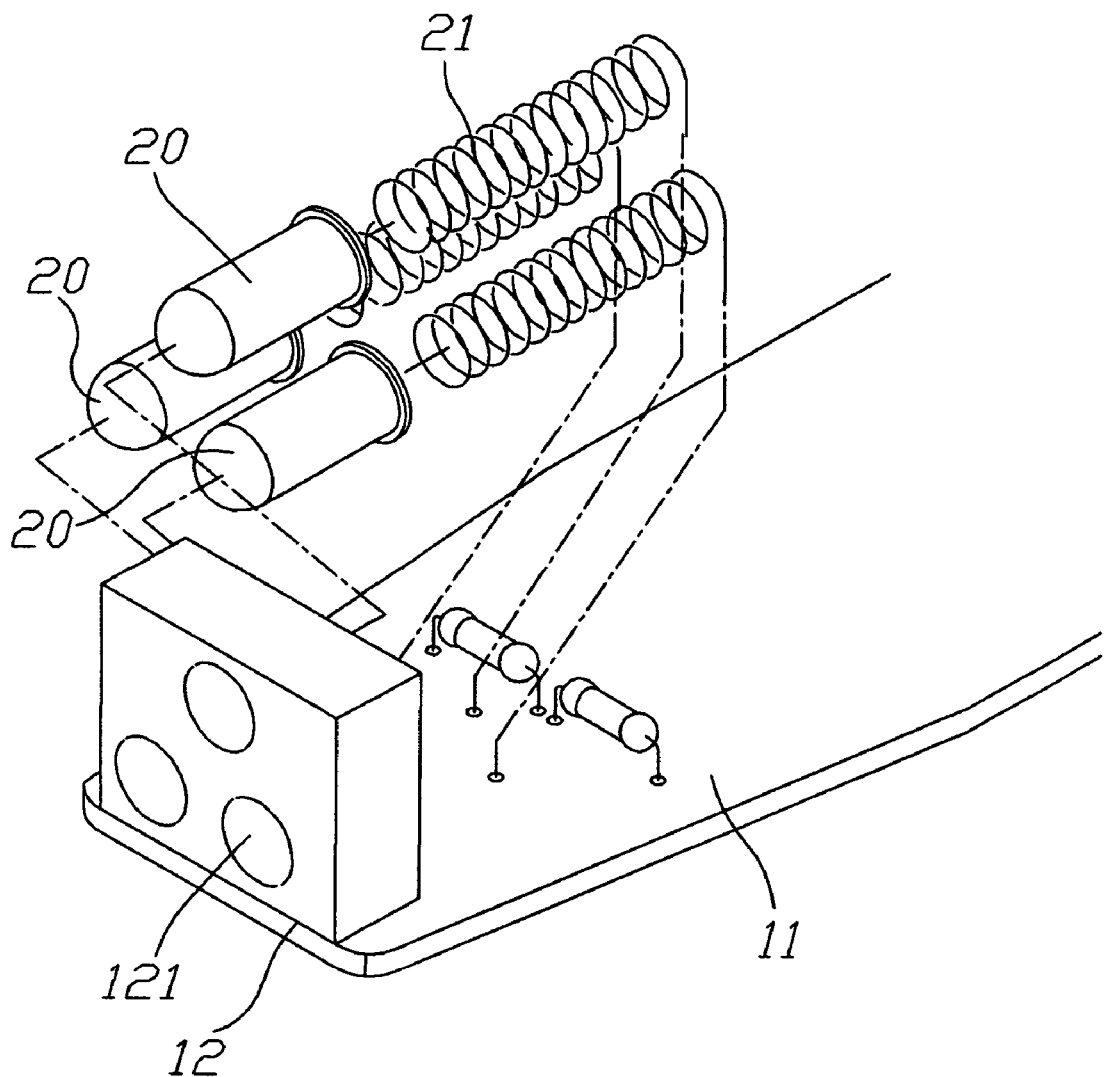
FIG. 5 is a cross-sectional diagram of the electrode being installed onto the casing according to another preferred embodiment of this invention.
Figure 6:
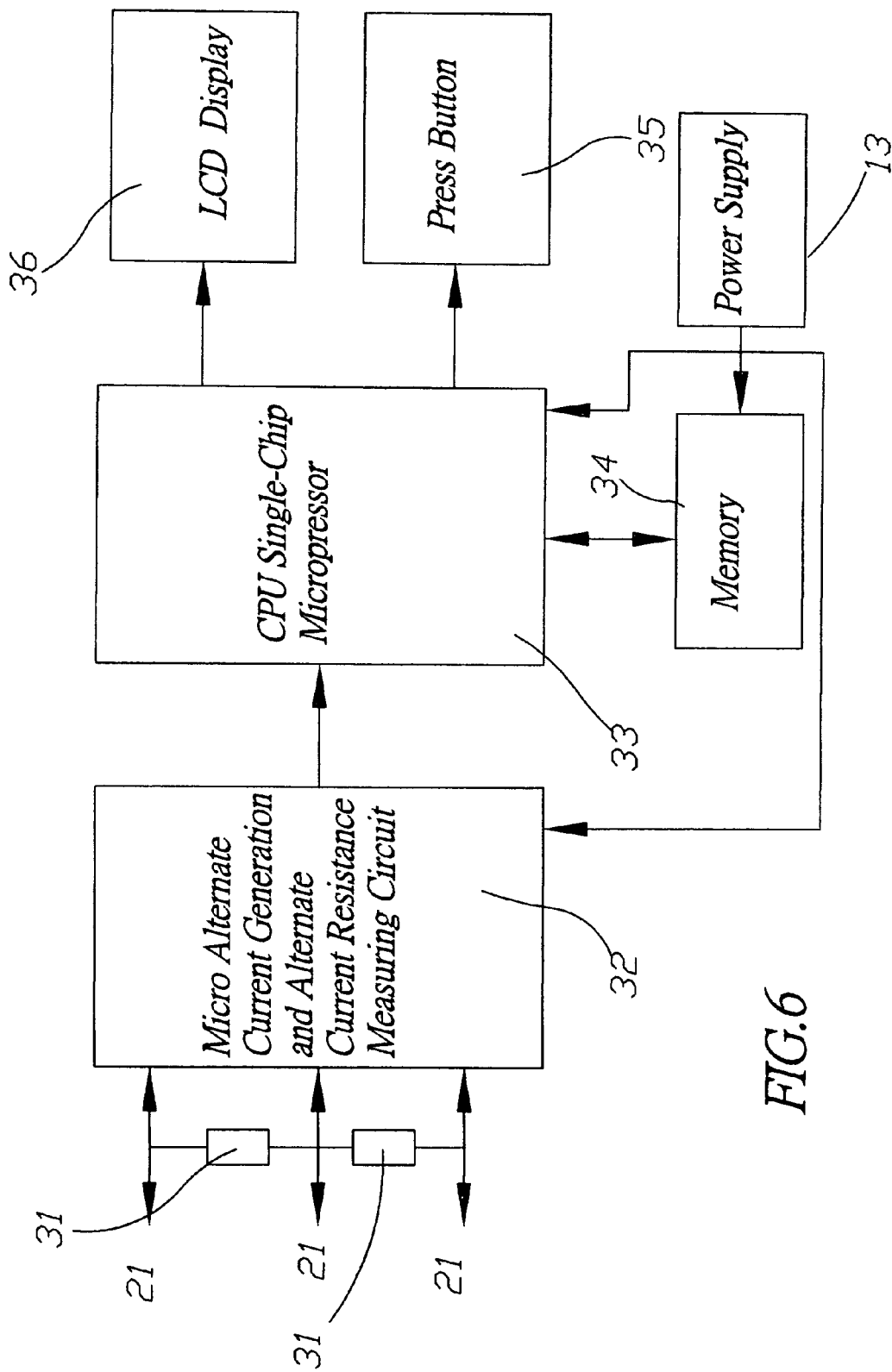
FIG. 6 is the block diagram of the circuit of the present invention.
Figure 7:
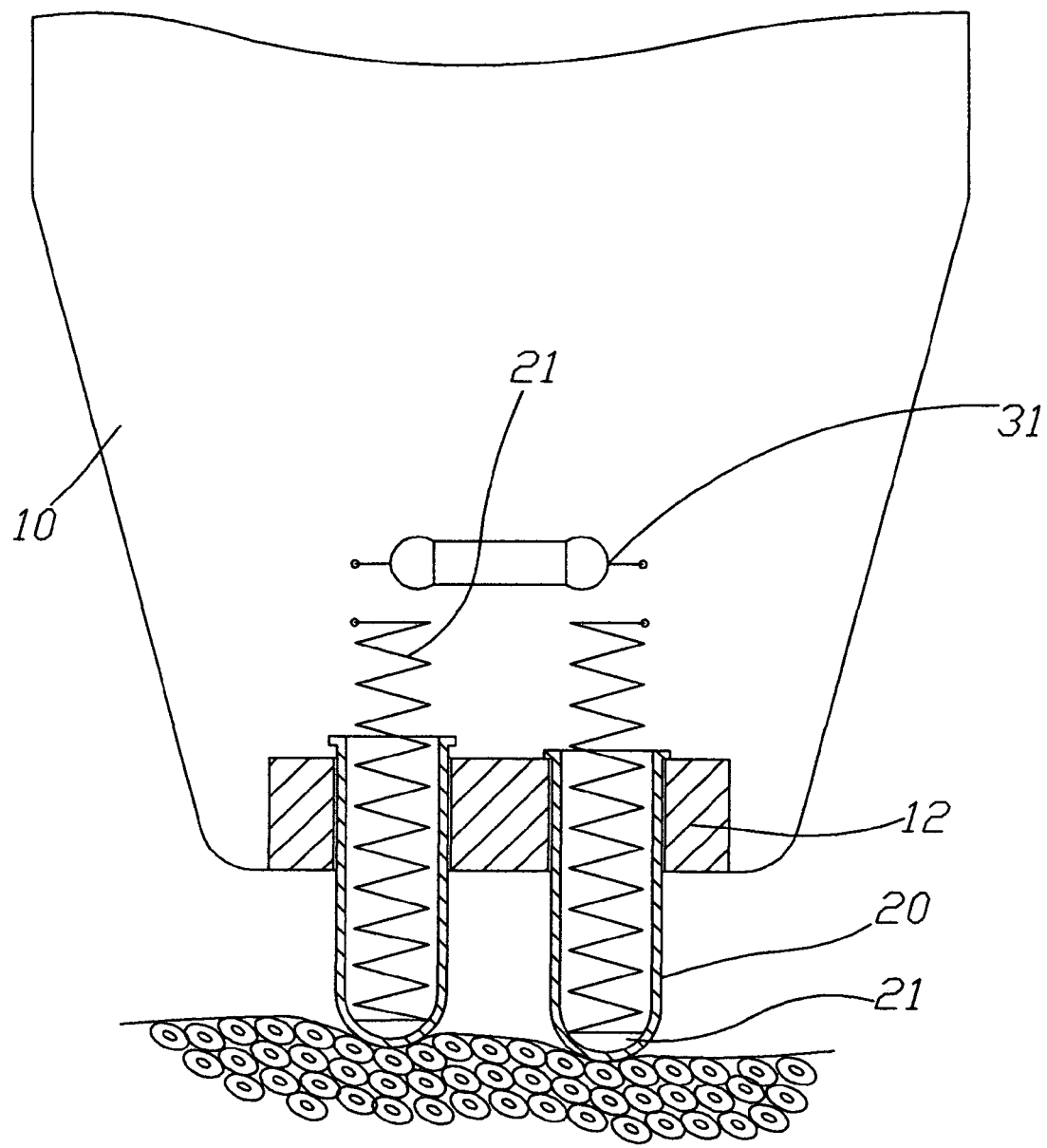
FIG. 7 is an illustrative diagram of the electrode being pressed onto the skin according to the present invention.

Please refer to FIGS. 2 to 6 for the apparatus for testing skin moisture. Such apparatus comprises a casing 10 (as shown in FIG. 4) having a bottom panel 11; a fixed base 12 (which is a block in this embodiment) at the front end of the bottom panel 11; at least one through hole 121 on the fixed base 12 (2 or 3 through holes are used in this embodiment) as shown in FIGS. 2 and 5, and the through hole 121 respectively passes through an electrically conductive hollow cylindrical electrode 20 with one closed end, and such electrode 20 contains an electrically conductive elastic member 21, and the other end of such elastic member 21 is connected to a micro alternate current generator and an alternate current resistance testing circuit 32 (as shown in FIG. 6) and then fixed onto the bottom panel 11. Further, the electrode 20 at its open end has a flange 22 extended outwardly, and the area of the flange 22 is larger than that of the through hole 121, so that when the electrode 20 passes through the through hole 121, the flange 22 blocks the electrode 20 and prevents it from falling out from the fixed base 12.

Further, please refer to FIGS. 4 and 6. The casing 10 has a power supply 13 which is a battery in this embodiment, and the power supply 13 is converted into a micro alternate current by the micro alternate current generator and the alternate current resistance testing circuit 32, and the micro alternate current generator and the alternate current resistance testing circuit 32 has a parallel correction resistor 31 (as shown in FIG. 6) on the circuit connected to the micro alternate current generator and the alternate current resistance testing circuit 32. Further, the micro alternate current generator and the alternate current resistance testing circuit 32 is connected to a CPU single-chip microprocessor 33, and the CPU single-chip microprocessor 33 is connected respectively to a memory 34, a display device 36 and a press button 35 exposed to the exterior of the casing 10, wherein the memory 34 stores the statistical database of the data measured in the test, and the display device 36 is a liquid crystal display (LCD) screen in this embodiment, and the press button 35 is used to control the switching of operation modes.

Please refer to FIGS. 2 to 6. A user may press down the press button 36 to start the test of this invention. The user should not touch skin to be tested with the apparatus right away. First, allow the power of the power supply be converted into a micro alternate current to pass through the electrodes 20 and the correction resistor 31 first. The display device 36 shows the measured resistance, so that the user can make any necessary correction for the difference caused by variable factors such as voltage and ambient temperature.

Since the theory of the operation of this invention resides on the human skin being composed of moisture, grease, and other colloid (which is a type of proteins), wherein the conductivity of the water is high, and the other constituents such as grease is less conductive. In addition, a cell composed of cytoplasm and lymph around the cell is more conductive, but the cell membrane is an insulator, and constituting a capacitance structure. Further, two electrodes or a multiple of electrodes with constant pressure on the skin surface can measure the AC conductive resistance in order to measure the water content of the skin. Therefore, when the electrode 20 presses onto the testing skin, the testing skin will send the test result from the electrode 20 to the correction resistor 31, and the resistance is measured by the micro alternate current generator and the alternate current resistance testing circuit 20. The measured result will be sent to the CPU single-chip microprocessor 33. The CPU single-chip microprocessor 33 will retrieve the data from the memory 34 for the comparison, and the result of the comparison will be sent to the display device 26 for display, therefore the user can know about the water content of the testing skin.

In the test process, we must keep an objective capacitor, and the conditions to keep an objective capacitor include:
1. the pressure exerted on the skin;
2. the size of the electrode; and
3. the feature of the skin.

The size of the electrode as listed above can be adjusted to a fixed size easily. Therefore, it is then necessary to control the pressure exerted on the skin for the skin moisture. When the electrode 20 is pressed onto the skin to exert a force on the elastic member 21, the limitation of the fixed base 21 can keep the same moving distance of the electrode 20 for each time, and thus having the same pressure exerted on the electrode 20 by the elastic member and the same pressure exerted on the skin by the electrode 20. Therefore, this invention gives the same test result for the tests under the same environment. Furthermore, this invention makes use of the electrode 20 to perform the test, and thus the cost is much lower than the conventional instrument.

In summation of the above description above, the present invention herein enhances the shape, structure, device, and performance over the conventional structure and overcomes the shortcomings of the prior art, and complies with the requirements of environmental protection and recycle. The present invention further complies with the patent application requirements and is submitted to the Patent and Trademark Office for review and granting of the commensurate patent rights. and granting of the commensurate patent rights.

While the invention has been described by way of example and in terms of a preferred embodiment, it is to be understood that the invention is not limited thereto. To the contrary, it is intended to cover various modifications and similar arrangements and procedures, and the scope of the appended claims therefore should be accorded the broadest interpretation so as to encompass all such modifications and similar arrangements and procedures.

What is claimed is:

1. An apparatus for testing moisture in skin comprising:
    a) a casing having:
        i) a micro alternate current generator;
        ii) an alternate current resistance measuring circuit;
        iii) a memory storing a predetermined value;
        iv) a display device;
        v) a power supply; and
        vi) a CPU single-chip microprocessor connected to the micro alternate current generator, the alternate current resistance measuring circuit, the memory, power supply, and the display device;
    b) a fixed base located at a front end of the casing and having of at least two through holes;
    c) at least two conductive electrodes, one of the at least two conductive electrodes is inserted into each of the plurality of through holes of the fixed base from an interior of the casing and protruding from the casing, each of the at least two conductive electrodes being movable between compressed and extended positions and having a flange limiting a length of outward movement in the extended position, the at least two conductive electrodes being connected in parallel to a correction resistor; and
    d) at least two elastic members, one of the at least two elastic members having a first end pressing outwardly against an interior of each of the at least two conductive electrodes and a second end connected to the micro alternate current generator and the alternate current resistance measuring circuit,
    wherein, when the electrodes engage the skin, the at least two elastic members providing a constant pressure between the skin and the at least two conductive electrodes, the CPU single-chip microprocessor receiving a measured result from the electrode least two electrodes and comparing the measured result with the predetermined value stored in memory and obtaining a compared result, and the display device displaying the compared result.

2. The apparatus according to claim 1, wherein each of the at least two elastic members is an electrically conductive spring.

3. The apparatus according to claim 1, wherein the display device is a liquid crystal display screen.

* * * * *